United States Patent
von Rheinbaben et al.

(10) Patent No.: US 6,551,553 B1
(45) Date of Patent: Apr. 22, 2003

(54) DISINFECTION METHOD

(75) Inventors: Friedrich von Rheinbaben, Duesseldorf (DE); Klaus-Peter Bansemir, Langenfeld (DE); Holger Biering, Grevenbroich (DE)

(73) Assignee: Ecolab GmbH & Co. oHG, Dusseldorf (DE)

( * ) Notice: Subject to any disclaimer, the term of this patent is extended or adjusted under 35 U.S.C. 154(b) by 0 days.

(21) Appl. No.: 09/402,410

(22) PCT Filed: Mar. 26, 1998

(86) PCT No.: PCT/EP98/01784

§ 371 (c)(1),
(2), (4) Date: Oct. 4, 1999

(87) PCT Pub. No.: WO98/44792

PCT Pub. Date: Oct. 15, 1998

(30) Foreign Application Priority Data

Apr. 4, 1997 (DE) .......................................... 197 13 849

(51) Int. Cl.[7] .................................................. A61L 2/00
(52) U.S. Cl. ................................ 422/28; 422/1; 422/13; 422/16; 422/17; 422/18; 422/19; 514/724
(58) Field of Search .............................. 422/1, 13, 15, 422/16, 17, 18, 19, 28; 514/724, 557, 558

(56) References Cited

U.S. PATENT DOCUMENTS

| 5,122,541 A | * | 6/1992 | Eggensperger et al. ..... 514/578 |
| 5,190,956 A | * | 3/1993 | Afonso et al. ............... 514/312 |
| 5,192,758 A | * | 3/1993 | DiNinno et al. ............ 514/210 |
| 5,728,404 A | * | 3/1998 | von Rheinbaben et al. . 424/642 |

FOREIGN PATENT DOCUMENTS

| DE | 42 21 743 | * | 1/1994 | |
| EP | 0079579 | * | 11/1982 | ............. A23L/3/34 |
| EP | 0 079 579 | * | 5/1983 | |
| JP | 07 298862 | * | 11/1995 | |
| JP | 7-298862 A | * | 11/1995 | |
| WO | WO93/16597 | * | 9/1993 | |

OTHER PUBLICATIONS

Patent Abstracts of Japan, vol. 96, No. 3 (1996).*
Journal of Food Protection, vol. 47, 11, Pgs. 841–847.*
Jap. Ass. Infec. Dis., vol. 55, Pgs. 355–366.*

* cited by examiner

Primary Examiner—Krisanne Thornton
(74) Attorney, Agent, or Firm—Merchant & Gould P.C.

(57) ABSTRACT

A process is provided for disinfecting articles at temperatures below 5° C. with an aqueous alcoholic salt solution. The process provides a fast reduction of microorganisms at low temperatures with a wide degree of efficacy.

10 Claims, No Drawings

DISINFECTION METHOD

BACKGROUND OF THE INVENTION

1. Field of the Invention

This application is filed under 35 U.S.C. 371 and based on PCT/EP98/0178, filed Mar. 26, 1998.

This invention relates to a process for disinfecting articles at low temperatures using liquid microbicidal preparations.

2. Discussion of Related Art

The effectiveness of conventional chemical disinfectants is dependent not only on the contact time and concentration, but also to a large extent on the contact temperature. Studies in this field have been conducted inter alia by P. Gelinas et al. (see *Journal of Food Production*, Vol. 47, No. 11, pages 841–847 (1984)) and by N. Noda et al. (see *J. Jap. Ass. Infect. Dis.*, Vol. 55, 355–366 (1981)). In many cases, it has also been found that the reduction in effectiveness at low temperatures cannot be reversed by higher concentrations of active substance even if this were acceptable from the toxicological point of view. Accordingly, many substances active as microbicides at room temperature are totally unsuitable as active substances for use at low temperatures. In general, only powerful oxidizing agents, such as hypochlorite and peracetic acid, can be used at temperatures of the order of 5° C. However, these active substances are also unsuitable for many applications, for example for the disinfection of sensitive materials, on account of their corrosiveness. Accordingly, efforts have long been made to find active substances or combinations of active substances that are safe and effective without any harmful side effects for the purpose of disinfection at low temperatures, more especially at temperatures below freezing point.

The present invention represents a major improvement in this field.

DESCRIPTION OF THE INVENTION

The present invention relates to a process for disinfecting articles in which the articles are treated with an aqueous alcoholic salt solution at temperatures below 5° C. In general, the treatment is even effective at temperatures of 0° C. or lower, in most cases at temperatures below –10° C. and even at temperatures below –50° C. A particularly high degree of effectiveness is achieved if the salts are present in the disinfecting solution in such a quantity that the saturation limit is reached or exceed at the in-use temperature. Effective disinfection is achieved both with the metal salts of organic acids and with the metal salts of inorganic acids.

It is particularly worth mentioning that the process according to the invention is effective against not just a few, but also against a very broad spectrum of microorganisms or viruses at the in-use temperatures. In addition, the disinfection process according to the invention is extremely kind to materials and the alcoholic aqueous salt solutions used for disinfection retain their effectiveness even after long periods of storage.

The process according to the invention may be applied on the one hand to articles which, by their nature, have to be kept cold and which must not be heated to room temperature or beyond with their destination in mind. Examples include the disinfection of surfaces in cold rooms, cold stores and refrigerated trucks and the disinfection of special laboratory equipment, such as refrigerated centrifuges and freezers. However, the disinfection of deep-frozen or refrigerated foods also counts as a special field in this regard. The new disinfection process is also suitable for articles which, in order to prevent material damage, should not be brought into contact with conventional disinfectants at room temperature or higher temperatures. In their case, material damage can be suppressed to a considerable extent by the new process without any reduction in the effectiveness of disinfection by carrying out the disinfection process at low temperatures.

The new process is characterized by the simultaneous presence of lower alcohols and salts, which must be at least partly water-soluble, in the aqueous disinfection liquid. Although liquids with this composition have already been used for disinfection at normal temperature, cf. for example patent applications WO 93/16597, DE 42 21 743 and EP 79 579, the fact that articles can be disinfected with the compositions described therein at low temperatures, more particularly at low temperatures below 0° C., has only just now been discovered. The fact that the microbicidal effect of aqueous alcoholic salt solutions does not weaken with decreasing temperature, but in some cases actually increases with decreasing temperature is extremely surprising in view of the dependence on temperature of other microbicidal agents.

The salts suitable for the process according to the invention should have a certain solubility in water which should amount to at least 0.1 g per liter and, more particularly, to more than 5 g per liter at 20° C. Both metal salts of inorganic acids and metal salts or organic acids are particularly suitable, the salts of hydrochloric acid, phosphoric acid and sulfuric acid being particularly suitable as the salts of inorganic acids. Some of these salts are also known in another context as Lewis acids. NaCl, but especially $K_3PO_4$, $Na_3PO_4$ and $ZnCl_2$ are mentioned as outstanding representatives of these salts. Of the organic salts, the metal salts of carboxylic acids containing 1 to 8 carbon atoms in the acid molecule are particularly suitable. Both in the case of the inorganic metal salts and in the case of the organic metal salts, salts of the alkali metals, alkaline earth metals and zinc are particularly preferred. Mixtures of several salts may of course also be used in the disinfecting solutions.

The concentration of salt in the solutions is preferably from 0.1 to 5% by weight, expressed as water-free salts and based on the final disinfecting solution. In a particularly preferred embodiment, the salts are used in the disinfecting solutions in such a quantity that the saturation concentration is reached or even exceeded at the in-use temperature.

The alcohols used in the disinfecting solutions are primarily lower water-miscible alcohols, more particularly aliphatic monoalcohols, although it is also possible to use glycols and other liquid polyols and partial ethers thereof, for example ethylene glycol, propylene glycol, glycerol, butoxy-ethanol and methoxybutanol. Readily volatile alcohols, more especially alcohols containing 1 to 4 carbon atoms in the molecule, are particularly preferred, ethanol and n-propanol being most particularly preferred. Instead of individual alcohols, mixtures of two or more alcohols may of course also be used. Relatively small quantities of aliphatic alcohols, which have only limited solubility in water, may also be used in admixture with water-miscible alcohols. The concentration of alcohols in the disinfecting solution should preferably be from about 40 to about 98% by weight, based on the disinfecting solution as a whole. Alcohol concentrations of about 60 to about 90% by weight and, more particularly, about 70 to about 80% by weight in the disinfecting solution are particularly preferred.

Particularly in cases where they are to be used for disinfection at or above room temperature, the aqueous alcoholic salt solutions used in accordance with the invention may also contain other microbicides or virucides which are known to be suitable for use at such temperatures. These other microbicides or virucides include in particular quaternary ammonium compounds, hydrogen peroxide and other peroxidic compounds, aldehydes, phenols, aromatic alcohols, such as phenoxy-ethanol, inorganic acids and active halogen compounds. These active substances are used in the usual concentrations. In general, there is no danger of their disrupting the effect of the process according to the invention at low temperatures.

In addition, the disinfecting solutions used in accordance with the invention may contain the auxiliaries and additives generally present in aqueous disinfecting solutions providing they do not impair the effect of the process in any way. Examples of such auxiliaries and additives are wetting agents, hydrotropes, surfactants, corrosion inhibitors, dyes and fragrances. The concentrations in which they used are determined by the desired effect.

The preparation of the disinfecting solution does not present any problems. In general, the salt is first dissolved in water in the quantity necessary for the required concentration, after which the necessary quantity of alcohol is mixed in. If appropriate for faster dissolution, the disinfecting solution may even be prepared at elevated temperatures. Other additives are generally added last to the solutions, although they may even be pre-dissolved in the initially purely aqueous solution or in the alcohol.

The treatment of the articles in the actual disinfection process is carried out, for example, by immersing the articles for a predetermined time in the cooled disinfecting bath or by applying the disinfecting solution to the cold articles, for example by spraying, brush-coating or by wiping the articles with an absorbent material impregnated with the disinfecting solution. The disinfecting solution may be applied to the articles both in pre-cooled form or, preferably, without cooling. The uncooled articles may also be treated with the disinfecting solution at around room temperature and then cooled with the adhering solution to the disinfection temperature over the contact time should this particular procedure appear appropriate for certain reasons, for example to prevent material damage. After disinfection, the disinfectant can be suitably removed from the articles. In many cases, however, there is no need to remove the disinfectant where residues of the disinfectant in or on the articles can be tolerated.

EXAMPLES

The microbicidal effect of the compositions used was tested both at room temperature (comparison) and at −20° C. and −70° C. In addition, salt-free alcoholic preparations were tested for comparison.

The virucidal activity was tested in accordance with the guidelines of the Bundesgesundheitsamt und die Deutsche Vereinigung zur Bekämpfung der Virukrankheiten (Zbl. Hyg. 1990: 189, 554–562), i.e. by the virus suspension test. To carry out the test, the disinfectant was mixed with the particular test virus suspension in a ratio of 9:1 and, at the end of the test period, a sample was removed from the mixture for virus titration. In cases where the suspension test was carried out with an additional protein challenge, the mixing ratio was 8:1:1 (disinfecting solution:protein solution: virus suspension).

The following virus suspensions were used:

Polio virus type I, strain Mahoney (grown and titrated on Rhabdomyosarcoma cells)

Adeno virus type 2, strain Adenoid 6 (grown and titrated on Hela cells)

Herpes simplex virus, type 1 (grown and titrated on Vero cells)

Vaccinia virus (grown on Vero cells)

Simian virus 40, strain 777 (grown and titrated on $CV_1$ cells).

In every case, the disinfecting solution and the virus suspension were mixed at room temperature (total volume 100 microliters) in Eppendorf vessels. Immediately afterwards, the test tubes were suddenly cooled to the contact temperature by immersion in a cooling bath. After the designated contact time at that temperature, the samples were reheated to room temperature. Virus detection was then carried out by microtitration using the above-mentioned cell lines after a dilution series corresponding to the progression 1:10, 1:100, 1:1000 etc. had been prepared.

The microbicidal activity of the compositions used in accordance with the invention was tested by the suspension test as specified in the Richtlinie für die Prüfung und Bewertung chemischer Desinfektions-verfahren, 12.07.1991, published by the Desinfektionsmittel-Kommission der Deutschen Gesellschaft für Hygiene und Mikrobiologie (DGHM) (mhp-Verlag, Ostring 13, 6200 Wiesbaden). The following test organisms were used:

| | | |
|---|---|---|
| *Staphylococcus aureus* | ATCC | 6538 |
| *Mycobacterium terrae* | ATCC | 15755 |
| *Candida albicans* | ATCC | 10231 |

The following Table shows the test results for 12 different formulations at different temperatures and with different contact times. The figures indicate in logarithmic units ($\log_{10}$) the reduction factors for the content of microorganisms and viruses after the particular contact times.

The test results show that the aqueous alcoholic salt solutions used in accordance with the invention retain a broad action spectrum to far below the freezing point.

TABLE

Virucidal and microbicidal activity

| No. | Formulation | Temp. in ° C. | Virus/test germ | RF/CT 1 min. | RF/CT 5 mins. | RF/CT 15 mins. | RF/CT 60 mins. |
|---|---|---|---|---|---|---|---|
| 1 | 5.0 g NaCl 74.5 ml ethanol (96%) dist. water to 100 ml* | −20 | Staph. aur. | | >5.95 | >6.02 | >5.95 |
| | | −20 | Cand. alb. | | >4.3 | >4.3 | >4.3 |
| | | −20 | Myc. ter. | | >5.3 | >5.3 | >5.3 |
| | | −20 | Polio | | 4.9 | 5.3 | ≧5.5 |
| | | −70 | | | | | ≧6.5 |
| | | RT | | | | | ≧6.5 |
| | | −20 | Adeno | | ≧4 | ≧4 | ≧4 |
| | | −20 | HSV | | ≧4.5 | ≧4.5 | ≧4.5 |
| | | RT | Vaccinia | ≧3 | | | ≧3 |
| | | −20 | | | | | ≧3 |
| | | −70 | | | | | ≧3 |
| | | RT | SV40 | ≧3.5 | | | ≧3.5 |
| | | −20 | | | | | ≧3.5 |
| | | −70 | | | | | ≧3.5 |

TABLE-continued

Virucidal and microbicidal activity

| No. | Formulation | Temp. in °C. | Virus/test germ | RF/CT 1 min. | RF/CT 5 mins. | RF/CT 15 mins. | RF/CT 60 mins. |
|---|---|---|---|---|---|---|---|
| 2 | 5.0 g NaCl | −20 | Staph. aur. | | >5.95 | >6.02 | >5.95 |
| | 0.5 g Tween 80+ | −20 | Cand. alb. | | >4.3 | >4.3 | >4.3 |
| | 1.43 g H₂O₂ (70%) | −20 | Myc. ter. | | >5.3 | >5.3 | >5.3 |
| | 74.5 ml ethanol (96%) | −20 | Polio | | 4.5 | 4.5 | 5 |
| | dist. water to 100 ml | −20 | Adeno | | ≧4 | ≧4 | ≧2 |
| | | −20 | HSV | | ≧4.5 | ≧4.5 | ≧4.5 |
| 3 | 0.1 g NaCl | RT | Polio | | 4 | 4 | |
| | 0.5 g Tween 80+ | −20 | | | 3.6 | 4.4 | |
| | 1.43 g H₂O₂ (70%) | | | | | | |
| | 74.5 ml ethanol (96%) | | | | | | |
| | dist. water to 100 ml | | | | | | |
| 4 | 5.0 g trisodium phosphate | −20 | Staph. aur. | | >5.95 | >6.02 | >5.95 |
| | 74.5 ml ethanol (96%) | −20 | Cand. alb. | | >4.3 | >4.3 | >4.3 |
| | dist. water to 100 ml* | −20 | Myc. ter. | | >5.3 | >5.3 | >5.3 |
| | | RT | Polio | 5.9 | | | >6.5 |
| | | −20 | | | 3.9 | 3.9 | >6.5 |
| | | −70 | | | | | >6.5 |
| | | RT | Adeno | >4 | | | ≧4 |
| | | −20 | | | ≧4 | ≧4.5 | ≧4 |
| | | −70 | | | | | ≧4 |
| | | −20 | HSV | | ≧4 | ≧4.5 | ≧4.5 |
| | | RT | Vaccinia | >3 | | | ≧3 |
| | | −20 | | | | | ≧3 |
| | | −70 | | | | | ≧3 |
| | | RT | SV40 | >3.5 | | | >3.5 |
| | | −20 | | | | | >3.5 |
| | | −70 | | | | | >3.5 |
| 5 | 5.0 g trisodium phosphate | RT | Polio | 3.7 | | | 7 |
| | 50 ml ethanol (96%) | −20 | | | | | 4.5 |
| | 30 ml n-propanol | −70 | | | | | 4.1 |
| | dist. water to 100 ml* | RT | Adeno | >4 | | | >4 |
| | | −20 | | | | | >4 |
| | | −70 | | | | | >4 |
| 6 | 5.0 g trisodium phosphate | RT | Polio | 4.5 | | | 7 |
| | 60 ml ethanol (96%) | −20 | | | | | 4.9 |
| | 20 ml n-propanol | −70 | | | | | 5 |
| | dist. water to 100 ml* | RT | Adeno | >4 | | | >4 |
| | | −20 | | | | | >4 |
| | | −70 | | | | | >4 |
| 7 | 5.0 g trisodium phosphate | RT | Polio | >6.6 | | | >6.6 |
| | 0.5 g Tween 80+ | −20 | | | 5.4 | | 5.3 |
| | 74.5 ml ethanol (96%) | RT | SV40 | ≧4.1 | | | ≧4.1 |
| | dist. water to 100 ml* | −20 | | | ≧3.5 | | ≧4.5 |
| | | RT | Adeno | >5.5 | | | >5.5 |
| | | −20 | | | >5.5 | | >5.5 |
| 8 | 5.0 g trisodium phosphate | −20 | Staph. aur. | | >5.95 | >6.02 | >5.95 |
| | 0.5 g Tween 80+ | −20 | Cand. alb. | | >4.3 | >4.3 | >4.3 |
| | 1.43 g H₂O₂ (70%) | −20 | Myc. ter. | | >5.3 | >5.3 | >5.3 |
| | 74.5 ml ethanol (96%) | −20 | Polio | | 4 | 3.9 | 4.3 |
| | dist. water to 100 ml* | −20 | Adeno | | ≧2 | n.a. | ≧2 |
| | | −20 | HSV | | ≧4.5 | ≧4.5 | ≧4.5 |
| 9 | 0.1 g tripotassium phosphate | RT | Polio | | 4.4 | | 5 |
| | | −20 | | | 3.5 | | 4.8 |
| | | −20** | | | 4 | | 3.9 |
| | 74.5 ml ethanol (96%) | −20*** | | | 4.5 | | 4.5 |
| | dist. water to 100 ml | | | | | | |
| 10 | 0.1 g tripotassium phosphate | RT | SV40 | | 2.6 | | ≧3.6 |
| | | −20 | | | 2.5 | | 3.3 |
| | 0.5 g Tween 80+ | RT | Adeno | | >5.5 | | >5.5 |
| | 74.5 ml ethanol (96%) | −20 | | | >5.5 | | >5.5 |
| | dist. water to 100 ml | | | | | | |
| 11 | 0.1 g tripotassium phosphate | RT | Polio | | 4.4 | | 4.5 |
| | | −20 | | | 4.3 | | 4.6 |
| | 0.5 g Tween 80+ | | | | | | |
| | 1.43 g H₂O₂ (70%) | | | | | | |
| | 74.5 ml ethanol (96%) | | | | | | |
| | dist. water to 100 ml | | | | | | |
| 12 | 0.5 g ZnCl₂ | RT | Polio | | ≧5.1 | | ≧5.1 |
| | 0.5 g Tween 80+ | −20 | | | 3.9 | | 4.4 |
| | | RT | SV40 | | 1.6 | | ≧3.6 |
| | 74.5 ml ethanol (96%) | −20 | | | 2.3 | | ≧3.5 |
| | dist. water to 100 ml* | RT | Adeno | | ≧4.5 | | ≧4.5 |
| | | −20 | | | ≧4.5 | | ≧4.5 |
| A | 74.5 ml ethanol (96%) | RT | Polio | | 0.4 | | 0.7 |
| | | −20 | | | 0 | | 0 |
| | dist. water to 100 ml | RT | SV40 | | 1.2 | | 2.1 |
| | | −20 | | | 1.3 | | 1.5 |
| B | 0.5 g Tween 80+ | RT | Polio | | 0.5 | | 1.1 |
| | | −20 | | | 0 | | 0 |
| | 74.5 ml ethanol (96%) | RT | SV40 | | 1.2 | | 1.9 |
| | dist. water to 100 ml | −20 | | | 1 | | 1.5 |

Abbreviations:
CT: contact time
FR: reduction factor
RT: room temperature
*With sediment
**Challenge with foetal calf serum
***Challenge with bovine serum albumin
+Tween 80 = ethoxylated sorbitan oleate (ICI)

What is claimed is:

1. A process for reducing population of a microorganism on an article comprising:

providing an aqueous alcoholic salt solution comprising:
70 to 80 wt-% alcohol; and
salt comprising:
alkali metal, alkaline earth metal, zinc, or mixture thereof; and
chloride, phosphate, sulfate, or mixture thereof;
the salt concentration being equal to or greater than the saturation level at temperature employed for contacting; and contacting the article with the solution at a temperature below 0° C.

2. The process of claim 1, wherein the salt comprises $K_3PO_4$, $Na_3PO_4$, $ZnCl_2$, or mixtures thereof.

3. The process of claim 1 wherein the aqueous alcoholic salt solution comprises 0.1 to 5 percent by weight of salt.

4. The process of claim 1 wherein the aqueous alcoholic salt solution comprises an alcohol having 1 to 4 carbon atoms.

5. The process of claim 4 wherein the aqueous alcoholic salt solution comprises ethanol, n-propanol or mixtures thereof.

6. The process of claim 1 wherein contact with the article occurs at temperatures below −10° C.

7. The process of claim 6 wherein contact with the article occurs at temperatures below −50° C.

8. The process of claim 1 wherein the contacted article comprises a virus.

9. The process of claim 1 wherein contact between the solution and the article comprises immersing said article in the solution for a pre-determined time, or applying said solution to articles at a temperature below 5° C.

10. The process of claim 9 wherein the solution is not cooled prior to application to the article.

* * * * *